(12) United States Patent
Ramin

(10) Patent No.: US 6,447,761 B1
(45) Date of Patent: Sep. 10, 2002

(54) COMPOSITION AND PROCESS FOR MAKING UP KERATINOUS SUBSTANCES IN RELIEF

(75) Inventor: Roland Ramin, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/524,571

(22) Filed: Mar. 13, 2000

(30) Foreign Application Priority Data

Mar. 11, 1999 (FR) .............................. 99 03006

(51) Int. Cl.$^7$ ................................ A61K 7/04
(52) U.S. Cl. ..................... 424/61; 424/401; 424/64; 424/69; 424/70.7; 424/78.08; 424/78.02; 424/78.03; 424/78.18; 424/70.3; 427/407.1; 106/415
(58) Field of Search .................... 424/401, 61, 63, 424/70.1, 78.02, 78.03, 78.08, 78.18, 69, 70.7, 64, 70.3; 427/407.1; 106/415

(56) References Cited

U.S. PATENT DOCUMENTS

| | | | | |
|---|---|---|---|---|
| 3,681,374 A | * | 8/1972 | Yano et al. ................. | 260/308 |
| 4,158,053 A | | 6/1979 | Greene et al. ............... | 424/61 |
| 4,822,423 A | | 4/1989 | Soyama et al. .............. | 106/5 |

FOREIGN PATENT DOCUMENTS

| | | |
|---|---|---|
| EP | 0 679 698 | 11/1995 |
| EP | 0797977 A1 * | 10/1997 |
| FR | 2 578 741 | 9/1986 |
| FR | 2 757 049 | 6/1998 |
| FR | 2 757 050 | 6/1998 |
| FR | 2 757 052 | 6/1998 |

OTHER PUBLICATIONS

English language Derwent Abstract of EP 0 679 698.
English language Derwent Abstract of FR 2 757 049.
English language Derwent Abstract of FR 2 757 050.
English language Derwent Abstract of FR 2 757 052.

* cited by examiner

Primary Examiner—Thurman K. Page
Assistant Examiner—Liliana Di Nola-Baron
(74) Attorney, Agent, or Firm—Finnegan, Henderson, Farabow, Garrett & Dunner LLP

(57) ABSTRACT

A cosmetic make-up composition containing, in a cosmetically acceptable medium, a film-forming polymer and a coloring material containing at least one colored polymer film fragment which exhibits two substantially flat faces, the fragment being insoluble in the medium of the composition. A make-up kit containing a first composition containing a film-forming polymer and a second composition containing a film-forming polymer and a colored film fragment. A cosmetic process for making up keratinous substances. The make-up obtained from the process exhibits a grainy effect.

68 Claims, No Drawings

COMPOSITION AND PROCESS FOR MAKING UP KERATINOUS SUBSTANCES IN RELIEF

The present invention relates to a cosmetic composition for the grainy making up of keratinous substances comprising a film-forming polymer and particles, and to a make-up kit comprising the composition. Another subject matter of the invention is a cosmetic process for making up keratinous substances. The composition according to the invention can be applied to the nails, to the skin, both of the face and of the body, including the lips, and to the hair, in particular of human beings. More specifically, the invention relates to a nail varnish.

The make-up composition can be a nail varnish, a face powder, an eye shadow, a foundation, and a make-up product for the lips or a product for making up the body. The composition can also be applied to make-up accessories, such as false nails, false eyelashes, false wigs, or to discs or patches, which adhere to the skin or lips (of the beauty spot type).

Nail varnish compositions generally comprise a film-forming polymer, either dissolved in an organic solvent or dispersed in the form of particles in an aqueous medium, and a colouring material, in particular a pigment. Such varnishes are disclosed, for example, in U.S. Pat. No. 4,158,053 and French Patent No. 2,578,741, the disclosures of both of which are hereby incorporated by reference.

These nail varnishes, after application to the nail of one or more layers of the composition and after drying, generally result in the formation of a glossy or matt, smooth, continuous and homogeneous film. Some films also exhibit good cosmetic smooth, continuous and homogeneous film. Some films also exhibit good cosmetic properties, such as good hold, and in particular good adhesion to the nail and good resistance to water, to rubbing movements and to impacts.

With changing fashion, consumers, who are increasingly demanding, are looking for novel make-up products that confer original or specific make-up effects. A need therefore remains to have available a make-up product which, when applied to a substrate, such as human nails, skin or hair, results in a make-up effect different from those of the smooth, continuous and homogeneous films currently obtained with the commercially available products.

An aim of the present invention is therefore to provide a make-up composition that makes it possible to obtain an in-relief make-up on keratinous substances while exhibiting good hold over time. The make-up confers a grainy or "roughcast" appearance on the substrate where it is applied.

The Inventor has found that a novel type of make-up for keratinous substances can be obtained by using a film-forming composition comprising specific fragments of colored film.

More specifically, an embodiment of the invention is a cosmetic make-up composition comprising, in a cosmetically acceptable medium, a film-forming polymer and a coloring material, wherein the coloring material comprises a colored polymer film fragment which exhibits two substantially flat faces, which has a thickness ranging from 40 to 200 $\mu$m and which has a larger dimension ranging from 0.1 to 4 mm, the fragment being insoluble in the medium of the composition.

When the composition is applied to keratinous substances, such as the nails, the film fragments are easily distributed in the deposited layer and are arranged well in the thickness of the layer. This composition provides a make-up film exhibiting parts, distributed randomly at the surface of the film, which are thicker than the mean thickness of the film. The surface of the make-up film exhibits a noncontinuous relief that is resistant to rubbing movements. An original in-relief make-up, original both to the touch and to the eye, is thus obtained which exhibits good adhesion to the made-up substrate and good hold.

This composition can advantageously be applied as a surface product, commonly known as a top coat.

Another embodiment of the invention is a cosmetic process for making up keratinous substances which comprises applying, to the keratinous substances, a composition as defined above.

Another embodiment of the invention is a cosmetic process for making up keratinous substances which comprises applying, to the keratinous substances, a first layer, also known as the base layer, of a first cosmetic composition comprising, in a cosmetically acceptable medium, a first film-forming polymer and in then applying, to at least a portion of the first layer, a second layer, also known as the surface layer, of a second cosmetic composition comprising, in a cosmetically acceptable medium, at least one second film-forming polymer and at least one colored polymer film fragment which exhibits two substantially flat faces, which has a thickness ranging from 40 to 200 $\mu$m and which has a larger dimension ranging from 0.1 to 4 mm, the fragment being insoluble in the medium of the composition, the first composition not comprising a polymer film fragment as present in the second composition.

Another embodiment of the invention is a make-up kit comprising:
  a first cosmetic composition (base layer composition) comprising, in a cosmetically acceptable medium, a first film-forming polymer;
  a second cosmetic composition (surface layer composition) comprising, in a cosmetically acceptable medium, at least one second film-forming polymer and at least one colored polymer film fragment which exhibits two substantially flat faces, which has a thickness ranging from 40 to 200 $\mu$m and which has a larger dimension ranging from 0.1 to 4 mm, the fragment being insoluble in the medium of the composition, wherein the first composition does not comprise a polymer film fragment as present in the second composition.

Another embodiment of the invention is a made-up substrate comprising a make-up capable of being obtained according to the process as defined before and applied on said substrate.

The colored polymer film fragment can be obtained from radical polymers and in particular from vinyl polymers, such as acrylic polymers or polymers based on poly(vinyl acetate), styrene-acrylic, vinyl/versatate or vinyl/ethylene copolymers, or vinyl/versatate/acrylate or vinyl/ethylene/chloride terpolymers. Use is preferably made of styrene/acrylic copolymers.

The color of the film fragment is not critical and can be chosen from all possible colorings. Use may in particular be made of a mixture of film fragments with different colorings. The film fragment can also comprise a different color on each face, as disclosed in European Patent Application No. EP-A-679,698, the disclosure of which is hereby incorporated by reference.

The thickness of the film fragment can preferably range from approximately 70 $\mu$m to approximately 130 $\mu$m and better still from approximately 90 $\mu$m to approximately 110 $\mu$m.

The larger dimension of the film fragment, measured in the plane passing through one of the two flat faces of the film fragment, can preferably range from 0.1 mm to 2 mm and better still from 0.1 mm to 1 mm.

The fragmented film is preferably matt and therefore does not exhibit a sparkling or glossy effect. The fragmented film can advantageously have a gloss, measured using a Byk-Gardner glossmeter at a light beam angle of 60°, of less than or equal to 15, in particular from 3 to 15, and in particular ranging from 3 to 10.

The film fragment can be colored using pigments or dyes. Mention may be made, as pigment, of inorganic pigments, organic pigments, pearlescent agents or metal powders.

The film fragment can additionally comprise at least one filler, which makes it possible, in particular, to obtain a film having the desired physicochemical properties. Mention may be made, as filler, of calcium carbonate, magnesium carbonate, carbonate of lime, barium sulphate, talc or kaolin.

According to the invention, the colored film fragment can be present, in particular in the surface composition, in an amount preferably ranging from 0.5% to 30% by weight with respect to the total weight of this surface composition, more preferably from 3% to 20% by weight and better still from 5% to 15% by weight.

The company Quadra Industries sells colored film fragments used according to the invention in particular under the name MONOCOLOR.

According to the invention, the cosmetically acceptable medium of the compositions according to the invention can comprise an aqueous medium or an organic solvent medium. In particular, the first and second compositions can comprise, independently of one another, an aqueous medium or an organic solvent medium.

Thus, according to a first alternative embodiment of the invention, the first and second compositions can comprise an aqueous medium, which is identical or different.

According to a second alternative embodiment of the invention, the first composition can comprise an aqueous medium and the second composition can comprise an organic solvent medium.

According to a third alternative embodiment of the invention, the first composition can comprise an organic solvent medium and the second composition can comprise an aqueous medium.

According to a fourth alternative embodiment of the invention, the first and second compositions can comprise an organic solvent medium, which is identical or different.

In the present application, the term "film-forming polymer" is understood to mean a polymer capable of forming an isolable film by itself alone or in the presence of an additional agent, which is able to form a film. The film-forming polymer of the base and surface compositions can be dissolved or dispersed in the form of particles in the corresponding cosmetically acceptable medium of each composition according to the invention. The film-forming polymer is therefore not present in the form of a film, which is already formed but, quite the contrary, in a form such that it will form a film after the application of the composition to the keratinous substances.

Representative film-forming polymers, which can be used in the compositions of the present invention, include synthetic polymers of radical type or of polycondensate type, polymers of natural origin and their mixtures. The first and second film-forming polymers of the first and second compositions can be identical or different.

The term "radical film-forming polymer" is understood to mean a polymer obtained by polymerization of monomers comprising unsaturation, in particular ethylenic unsaturation, each monomer being capable of homopolymerizing (unlike polycondensates). The film-forming polymers of radical type can be, in particular, vinyl polymers or copolymers, in particular acrylic polymers.

The vinyl film-forming polymers can result from the polymerization of monomers comprising ethylenic unsaturation having at least one acid group and/or esters of these acid monomers and/or amides of these acid monomers.

Use is preferably made of anionic radical film-forming polymers, that is to say polymers having at least one monomer comprising an acid group.

Use may be made, as monomer comprising an acid group, of α,β-ethylenic unsaturated carboxylic acids, such as acrylic acid, methacrylic acid, crotonic acid, maleic acid or itaconic acid. Use is preferably made of (meth)acrylic acid and crotonic acid and more preferably of (meth)acrylic acid.

The esters of acid monomers are advantageously chosen from esters of (meth)acrylic acid (also known as (meth) acrylates), in particular alkyl (meth)acrylates, especially ($C_1$–$C_{20}$) alkyl (meth)acrylates, preferably ($C_1$–$C_8$) alkyl (meth)acrylates, aryl (meth)acrylates, in particular ($C_6$–$C_{10}$) aryl (meth)acrylates, and hydroxyalkyl (meth)acrylates, in particular ($C_2$–$C_6$) hydroxyalkyl (meth)acrylates. Mention may be made, among alkyl (meth)acrylates, of methyl methacrylate, ethyl methacrylate, butyl methacrylate, isobutyl methacrylate, 2-ethylhexyl methacrylate and lauryl methacrylate. Mention may be made, among hydroxyalkyl (meth) acrylates, of hydroxyethyl acrylate, 2-hydroxypropyl acrylate, hydroxyethyl methacrylate and 2-hydroxypropyl methacrylate. Mention may be made, among aryl (meth) acrylates, of benzyl acrylate and phenyl acrylate.

The particularly preferred esters of (meth)acrylic acid are alkyl (meth)acrylates.

According to the present invention, the alkyl group of the esters can be either fluorinated or perfluorinated that is to say that a portion or all of the hydrogen atoms of the alkyl group are substituted by fluorine atoms.

Mention may be made, as amides of acid monomers, for example, of (meth)acrylamides, and in particular N-alkyl (meth)acrylamides, especially N-($C_2$–$C_{12}$ alkyl)(meth) acrylamides. Mention may be made, among N-alkyl(meth) acrylamides, of N-ethylacrylamide, N-(t-butyl)acrylamide and N-(t-octyl)acrylamide.

The vinyl film-forming polymers can also result from the homopolymerization or from the copolymerization of at least one monomer chosen from vinyl esters and styrene monomers. In particular, these monomers can be polymerized with acid monomers and/or their esters and/or their amides, such as those mentioned above. Mention may be made, as examples of vinyl esters, of vinyl acetate, vinyl neodecanoate, vinyl pivalate, vinyl benzoate and vinyl t-butylbenzoate. Mention may be made, as styrene monomers, of styrene and α-methylstyrene.

The list of the monomers given is not limiting and it is possible to use any monomer known to a person skilled in the art coming within the categories of acrylic and vinyl monomers (including monomers modified by a silicone chain).

Mention may be made, as a film-forming acrylic polymer in aqueous dispersion which can be used according to the invention, of those sold under the names NEOCRYL XK-90®, NEOCRYL A-1070®, NEOCRYL A-1090®, NEOCRYL BT-62®, NEOCRYL A-1079® and NEOCRYL A-523® by the company Zeneca or DOW LATEX 432® by the company Dow Chemical.

Mention may thus be made, among the polycondensates, which can be used as film-forming polymer, of anionic, cationic, non-ionic or amphoteric polyurethanes, of polyurethane-acrylics, of polyurethane-polyvinylpyrrolidones, of polyester-polyurethanes, of polyether-polyurethanes, of polyureas, of polyurea-polyurethanes, and of their mixtures.

The film-forming polyurethane can be, for example, an aliphatic polyurethane, a cycloaliphatic polyurethane, an aromatic polyurethane, a polyurea-polyurethane or a polyurea copolymer comprising, alone or as a mixture:

at least one sequence of aliphatic and/or cycloaliphatic and/or aromatic polyester origin, and/or, at least one branched or unbranched silicone sequence, for example polydimethylsiloxane or polymethylphenylsiloxane, and/or at least one sequence comprising fluorinated groups.

Mention may in particular be made, as film-forming polyurethane polymer in aqueous dispersion which can be used according to the invention, of the polyester-polyurethanes sold under the names AVALURE UR-405®, AVALURE UR-410®, AVALURE UR425® and SANCURE 2060® by the company Goodrich and the polyether-polyurethanes sold under the name SANCURE 878® by the company Goodrich and NEOREZ R 970® by the company ICI.

Mention may also be made, among film-forming polycondensates, of polyesters, polyesteramides, polyesters comprising a fatty chain, polyamides and epoxy ester resins, the resins resulting from the condensation of formaldehyde with an arylsulphonamide, or arylsulphonamide epoxy resins.

The polyesters can be obtained, in a known way, by polycondensation of dicarboxylic acids with polyols, in particular diols.

The dicarboxylic acid can be aliphatic, alicyclic or aromatic. Mention may be made, as examples of such acids, of oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalenedicarboxylic acid. These dicarboxylic acid monomers can be used alone or in combination with at least two dicarboxylic acid monomers. The choice is preferably made, among these monomers, of phthalic acid, isophthalic acid or terephthalic acid.

The diol can be chosen from aliphatic or alicyclic or aromatic diols. Use is preferably made of a diol chosen from ethylene glycol, diethylene glycol, triethylene glycol, 1,3-propanediol, cyclohexanedimethanol and 4-butanediol. Use may be made, as other polyols, of glycerol, pentaerythritol, sorbitol and trimethylolpropane.

The polyesteramides can be obtained in a way analogous to the polyesters by polycondensation of diacids with diamines or aminoalcohols. Use may be made, as diamine, of ethylenediamine, hexamethylenediamine and meta- or para-phenylenediamine. Use may be made, as aminoalcohol, of monoethanolamine.

The polyester can additionally comprise at least one monomer carrying at least one —$SO_3M$ group, with M representing a hydrogen atom, an ammonium ion $NH_4^+$ or a metal ion, such as, for example, a $Na^+$, $Li^+$, $K^+$, $Mg^{2+}$, $Ca^{2+}$, $Fe^{2+}$ and $Fe^{3+}$ ion. Use may in particular be made of a bifunctional aromatic monomer comprising such an —$SO_3M$ group.

The aromatic nucleus of the bifunctional aromatic monomer additionally carrying an —$SO_3M$ group as described above can be chosen, for example, from benzene, naphthalene, anthracene, diphenyl, oxydiphenyl, sulphonyl-diphenyl or methylenediphenyl nuclei. Mention may be made, as examples of bifunctional aromatic monomer additionally carrying an —$SO_3M$ group, of sulphoisophthalic acid, sulphoterephthalic acid, sulphophthalic acid and 4-sulphonaphthalene-2,7-dicarboxylic acid.

It is preferable to use, in the compositions which are the subject-matter of the invention, copolymers based on isophthalate/sulphoisophthalate and more particularly copolymers obtained by condensation of diethylene glycol, cyclohexanedimethanol, isophthalic acid and sulphoisophthalic acid. The company Eastman Chemical Products sells such polymers, for example, under the trade name EASTMAN AQ.

The optionally modified polymers of natural origin can be chosen from shellac resin, sandarac gum, dammars, elemis, copals, cellulose polymers, such as nitrocellulose, cellulose acetate, cellulose acetobutyrate, cellulose acetopropionate or ethyl cellulose, and their mixtures.

The film-forming polymer of the base and surface compositions can be generally present respectively at a content ranging from 1% to 70% by weight with respect to the total weight of the respective base and surface composition and better still ranging from 10% to 40% by weight.

Mention may be made, as organic solvent which can be used in the invention, of:

ketones which are liquid at room temperature, such as methyl ethyl ketone, methyl isobutyl ketone, diisobutyl ketone, isophorone, cyclohexanone or acetone;

alcohols which are liquid at room temperature, such as ethanol, isopropanol, diacetone alcohol, 2-butoxyethanol or cyclohexanol;

glycols which are liquid at room temperature, such as ethylene glycol, propylene glycol, pentylene glycol or glycerol;

propylene glycol ethers which are liquid at room temperature, such as propylene glycol monomethyl ether, propylene glycol monomethyl ether acetate or dipropylene glycol mono(n-butyl) ether;

short-chain esters (having a total of 3 to 8 carbon atoms), such as ethyl acetate, methyl acetate, propyl acetate, n-butyl acetate or isopentyl acetate;

ethers which are liquid at room temperature, such as diethyl ether, dimethyl ether or dichlorodiethyl ether;

alkanes which are liquid at room temperature, such as decane, heptane, dodecane or cyclohexane, aromatic cyclic compounds which are liquid at room temperature, such as toluene and xylene;

aldehydes which are liquid at room temperature, such as benzaldehyde or acetaldehyde; and their mixtures.

These solvents are more particularly suitable for making up the nails. A composition comprising these solvents then constitutes a nail varnish.

In each composition comprising an organic solvent medium, the organic solvent can be generally present at a content ranging from 30 to 99% by weight with respect to the total weight of each composition and preferably from 60% to 90% by weight.

When the compositions for the implementation of the process according to the invention comprise an aqueous medium, the latter can be composed essentially of water or alternatively of an aqueous/alcoholic mixture comprising in particular lower ($C_1$–$C_5$) monoalcohols. The content of water in each composition comprising an aqueous medium can generally range from 30 to 99% by weight with respect to the total weight of each composition and preferably from 60 to 90% by weight.

An additional agent which is able to form a film can be provided in order to improve the film-forming properties of the composition, in particular of the base and/or surface composition according to the invention.

Such an additional agent, which is able to form a film can be chosen from any compound known to a person skilled in the art as being capable of fulfilling the desired purpose and can be chosen in particular from plasticizing agents.

In addition, when the base and/or surface composition or one of the base and/or surface compositions according to the invention comprises a film-forming polymer in the form of particles dispersed in the corresponding medium of the composition, the additional agent which is able to form a film can also be chosen from coalescence agents.

Furthermore, the base and/or surface composition according to the invention can comprise additional coloring materials other than the film fragment described above. The coloring material can be chosen in particular from dyes (water-soluble or fat-soluble dyes) and pulverulent coloring materials, such as pigments, pearlescent agents or glitters, well known to a person skilled in the art. In particular, the pulverulent coloring materials can be chosen from those having a mean particle size of generally less than or equal to 70 $\mu$m, in particular ranging from 1 $\mu$m to 70 $\mu$m, and preferably of less than or equal to 50 $\mu$m, in particular ranging from 1 $\mu$m to 50 $\mu$m. The additional coloring materials can be present in each composition in an amount generally ranging from 0.01% to 15% by weight with respect to the total weight of each composition. These coloring materials can make it possible in particular to obtain a smooth make-up film, in contrast to the make-up film comprising the colored film fragment defined above.

According to a preferred embodiment of the make-up kit and process according to the invention, the base composition can comprise a coloring material comprising a water-soluble or fat-soluble dye and/or pulverulent coloring materials having a mean particle size of less than or equal to 70 $\mu$m and better still of less than or equal to 50 $\mu$m. In particular, the base composition can be colored and can be capable of forming a first colored film and the surface composition can comprise a substantially translucent medium so that the medium does not mask the color of the colored polymer film fragment. The application of the base composition to the keratinous substances and then of the surface composition then results in a make-up which clearly reveals the colored film fragments distributed randomly over the colored layer obtained with the base composition. A contrast between the colors of the film fragments and the color of the base layer is then observed. The base composition advantageously has a different color from those of the colored film fragments and optionally from that of the medium of the surface composition.

The base and surface compositions according to the invention can additionally comprise any additive known to a person skilled in the art as being capable of being incorporated in such a composition, such as thickening agents, spreading agents, wetting agents, dispersing agents, antifoaming agents, preservatives, UV screening agents, active principles, surfactants, moisturizing agents, fragrances, neutralizing agents, stabilizing agents or antioxidants. Of course, a person skilled in the art will take care to choose this or these optional additional compounds and/or their amounts so that the advantageous properties of the corresponding composition according to the invention are not, or not substantially, detrimentally affected by the envisaged addition.

The base and surface compositions according to the invention can be prepared by a person skilled in the art on the basis of his overall knowledge and according to the state of the art.

The base and surface compositions are advantageously packaged in separate compartments or containers accompanied by appropriate application means which are identical or different, such as brushes, pens or sponges.

The composition comprising the colored polymer film fragment can be applied either at one of the ends of the base layer or in the middle or non-continuously, in particular in the form of symmetrical or asymmetrical geometric designs (for example in the form of points, squares, circles or stars), distributed randomly or in an ordered way, with sharp or blurred outlines.

The invention is illustrated in more detail in the following examples.

EXAMPLE 1

| | |
|---|---|
| Nitrocellulose | 10 g |
| Plasticizers and resin | 15 g |
| Pyrogenic silica (AEROSIL 200 from Degussa) | 1.5 g |
| White particles in the form of fragmented film (MONOCOLOR WE 150/000 from Quadra) | 10 g |
| Ethyl acetate, butyl acetate q.s. for | 100 g |

The composition comprised a transparent medium in which the white-coloured fragmented film particles were dispersed.

After application of the composition to the nails, an in-relief make-up film was obtained exhibiting a non-continuous distribution of white particles. The make-up had a grainy appearance.

EXAMPLE 2

The two following nail varnish compositions A and B were prepared:

| | |
|---|---|
| Base composition A: | |
| Nitrocellulose | 19 g |
| N-Ethyl-o,p-toluenesulphonamide | 6 g |
| Tributyl acetylcitrate | 6 g |
| Black pigments | 1 g |
| Hectorite | 1.2 g |
| Isopropyl alcohol | 8 g |
| Ethyl acetate, butyl acetate q.s. for | 100 g |
| Surface composition B: | |
| Nitrocellulose | 10 g |
| Plasticizers and resin | 15 g |
| Pyrogenic silica (AEROSIL 200 from Degussa) | 1.5 g |
| White particles in the form of fragmented film (MONOCOLOR WE 150/000 from Quadra) | 3 g |
| Pink particles in the form of fragmented film (MONOCOLOR PEK 426/000 from Quadra) | 7 g |
| Ethyl acetate, butyl acetate q.s. for | 100 g |

A base layer with the composition A was applied to the nail, and then, after drying, a surface layer with the composition B was applied to the nail. An in-relief make-up with good hold was obtained exhibiting a non-continuous covering of white and pink particles on a black background. The make-up obtained has the appearance of a roughcast.

What is claimed is:

1. A cosmetic make-up composition comprising, in a cosmetically acceptable medium:
   a film-forming polymer and
   a coloring material,
   wherein the coloring material comprises at least one colored polymer film fragment which exhibits two substantially flat faces, which has a thickness ranging from 40 to 200 μm and which has a larger dimension ranging from 0.1 to 4 mm, the at least one colored polymer film fragment being insoluble in a medium of the composition.

2. The composition according to claim 1, wherein the at least one colored polymer film fragment has a thickness ranging from 70 μm to 130 μm.

3. The composition according to claim 2, wherein the at least one colored polymer film fragment has a thickness ranging from 90 μm to 110 μm.

4. The composition according to claim 1, wherein the at least one colored polymer film fragment has a gloss of less than or equal to 15.

5. The composition according to claim 4, wherein the at least one colored polymer film fragment has a gloss ranging from 3 to 10.

6. The composition according to claim 1, wherein the larger dimension of the at least one colored polymer film fragment ranges from 0.1 mm to 2 mm.

7. The composition according to claim 6, wherein the larger dimension of the at least one colored polymer film fragment ranges from 0.1 mm to 1 mm.

8. The composition according to claim 1, the at least one colored polymer film fragment results from a polymer film chosen from acrylic polymers, poly(vinyl acetate) polymers, styrene-acrylic, vinyl/versatate and vinyl/ethylene copolymers, and vinyl/versatate/acrylate and vinyl/ethylene/chloride terpolymers.

9. The composition according to claim 1, wherein the at least one colored polymer film fragment is present in an amount ranging from 0.5% to 30% by weight with respect to the total weight of the composition.

10. The composition according to claim 9, wherein the at least one colored polymer film fragment is present in an amount ranging from 3% to 20% by weight.

11. The composition according claim 1, wherein the cosmetically acceptable medium comprises an organic solvent medium or an aqueous medium.

12. The composition according to claim 1, wherein the film-forming polymer is chosen from radical polymers, polycondensates and polymers of natural origin.

13. The composition according claim 1, wherein the film-forming polymer is chosen from vinyl polymers, polyurethanes, polyesters and cellulose polymers.

14. The composition according to claim 1, wherein the film-forming polymer is present in the composition in an amount ranging from 1% to 70% by weight with respect to the total weight of the composition.

15. The composition according to claim 14, wherein the film-forming polymer is present in the composition in an amount ranging from 10% to 40% by weight with respect to the total weight of the composition.

16. The composition according to claim 1, further comprising an additional coloring material other than the at least one colored polymer film fragment.

17. The composition according to claim 16, wherein the additional coloring material is chosen from dyes and pulverulent coloring materials having a particle size of less than or equal to 70 μm.

18. The composition according to claim 1, further comprising at least one additive selected from additional agents which are able to form a film, thickening agents, spreading agents, wetting agents, dispersing agents, anti-foaming agents, preservatives, UV screening agents, active principles, surfactants, moisturizing agents, fragrances, neutralizing agents, stabilizing agents and antioxidants.

19. A nail varnish, face powder, eye shadow, foundation or product for making up the body comprising:
   a cosmetically acceptable medium:
   a film-forming polymer and
   a coloring material,
   wherein the coloring material comprises at least one colored polymer film fragment which exhibits two substantially flat faces, which has a thickness ranging from 40 to 200 μm and which has a larger dimension ranging from 0.1 to 4 mm, the at least one colored polymer film fragment being insoluble in a medium of the composition.

20. A cosmetic process for making up a keratinous substance comprising:
   applying, to the keratinous substance, at least one layer of a composition comprising, in a cosmetically acceptable medium:
   a film-forming polymer and
   a coloring material,
   wherein the coloring material comprises at least one colored polymer film fragment which exhibits two substantially flat faces, which has a thickness ranging from 40 to 200 μm and which has a larger dimension ranging from 0.1 to 4 mm, the at least one colored polymer film fragment being insoluble in a medium of the composition.

21. A cosmetic process for making up a keratinous substance, comprising applying to the keratinous substance:
   a first layer of a first composition comprising, in a cosmetically acceptable medium, a first film-forming polymer,
   and then, to at least a portion of the first layer, a second layer of a second composition comprising at least one second film-forming polymer in a cosmetically acceptable medium and at least one coloring material comprising at least one colored polymer film fragment which exhibits two substantially flat faces, which has a thickness ranging from 40 to 200 μm and which has a larger dimension ranging from 0.1 to 4 mm, the fragment being insoluble in the medium of the composition, wherein the first composition does not comprise the at least one colored polymer film fragment.

22. The process according to claim 21, wherein the at least one colored polymer film fragment has a thickness ranging from 70 μm to 130 μm.

23. The process according to claim 22, wherein the at least one colored polymer film fragment has a thickness ranging from 90 μm to 110 μm.

24. The process according to claim 21, wherein the at least one colored polymer film fragment has a gloss of less than or equal to 15.

25. The process according to claim 21, wherein the at least one colored polymer film fragment has a gloss ranging from 3 to 10.

26. The process according to claim 25, wherein the larger dimension of the at least one colored polymer film fragment ranges from 0.1 mm to 2 mm.

27. The process according to claim 21, wherein the larger dimension of the at least one colored polymer film fragment ranges from 0.1 mm to 1 mm.

28. The process according to claim 21, wherein the at least one colored polymer film fragment results from a polymer film chosen from acrylic polymers, poly(vinyl acetate) polymers, styrene-acrylic, vinyl/versatate and vinyl/ethylene copolymers, and vinyl/versatate/acrylate and vinyl/ethylene/chloride terpolymers.

29. The process according to claim 21, wherein the at least one colored polymer film fragment is present in the composition in an amount ranging from 0.5% to 30% by weight with respect to the total weight of the second composition.

30. The process according to claim 21, wherein the at least one colored polymer film fragment is present in the composition in an amount ranging from 3% to 20% by weight with respect to the total weight of the second composition.

31. The process according to claim 21, wherein at least one of the first composition and the second composition comprise an organic solvent medium or an aqueous medium.

32. The process according to claim 21, wherein the first film-forming polymer and the at least one second film-forming polymer are independently selected from radical polymers, polycondensates and polymers of natural origin.

33. The process according to claim 21, wherein the first polymer and the at least one second film-forming polymer are chosen, without distinction from one another, from vinyl polymers, polyurethanes, polyesters and cellulose polymers.

34. The process according to claim 21, wherein the first polymer is present in the first composition in an amount ranging from 1% to 70% by weight with respect to the total weight of the first composition.

35. The process according to claim 34, wherein the first polymer is present in the first composition in an amount ranging from 10% to 40% by weight with respect to the total weight of the first composition.

36. The process according to claim 21, wherein the at least one second film-forming polymer is present in the second composition in an amount ranging from 1% to 70% by weight with respect to the total weight of the second composition.

37. The process according to claim 36, wherein the at least one second film-forming polymer is present in the second composition in an amount ranging from 10% to 40% by weight with respect to the total weight of the second composition.

38. The process according to claim 21, wherein at least one of the first composition and the second composition additionally comprise at least one coloring material chosen from dyes and pulverulent coloring materials having a particle size of less than or equal to 70 µm.

39. The process according to claim 21, wherein the first composition comprises a coloring material comprising at least one of a dye and pulverulent coloring materials having a particle size of less than or equal to 70 µm.

40. The process according to claim 21, wherein the second composition comprises a substantially translucent medium.

41. The process according to claim 21, wherein at least one of the first composition and the second composition are applied to a substrate chosen from nails, cheeks, eyelids and body.

42. A make-up kit comprising a first compartment and a second compartment, wherein the first compartment comprises:
   a first composition comprising at least one first film-forming polymer in a cosmetically acceptable medium, and
   wherein the second compartment comprises:
      a second composition comprising at least one second film-forming polymer in a cosmetically acceptable medium and at least one coloring material comprising at least one colored polymer film fragment which exhibits two substantially flat faces, which has a thickness ranging from 40 to 200 µm and which has a larger dimension ranging from 0.1 to 4 mm, the at least one colored polymer film fragment being insoluble in the medium of the composition, and
   wherein the first composition does not comprise the at least one colored polymer film fragment present in the second composition.

43. The make-up kit according to claim 42, wherein the at least one colored polymer film fragment has a thickness ranging from 70 µm to 130 µm.

44. The make-up kit according to claim 43, wherein the at least one colored polymer film fragment has a thickness ranging from 90 µm to 110 µm.

45. The make-up kit according to claim 42, wherein the at least one colored polymer film fragment has a gloss of less than or equal to 15.

46. The make-up kit according to claim 45, wherein the at least one colored polymer film fragment has a gloss ranging from 3 to 10.

47. The make-up kit according to claim 42, wherein the larger dimension of the colored film fragment ranges from 0.1 mm to 2 mm.

48. The make-up kit according to claim 47, wherein the larger dimension of the colored film fragment ranges from 0.1 mm to 1 mm.

49. The make-up kit according to claim 42, wherein the at least one colored polymer film fragment results from a polymer film chosen from acrylic polymers, poly(vinyl acetate) polymers, styrene-acrylic, vinyl/versatate and vinyl/ethylene copolymers, and vinyl/versatate/acrylate and vinyl/ethylene/chloride terpolymers.

50. The make-up kit according to claim 42, wherein the at least one colored polymer film fragment is present in the second composition in an amount ranging from 0.5% to 30% by weight with respect to the total weight of the second composition.

51. The make-up kit according to claim 50, wherein the at least one colored polymer film fragment is present in the second composition in an amount ranging from 3% to 20% by weight with respect to the total weight of the second composition.

52. The make-up kit according to claim 42, wherein at least one of the first composition and the second composition comprises an organic solvent medium or an aqueous medium.

53. The make-up kit according to claim 42, wherein the first film-forming polymer and the at least one second film-forming polymer are independently selected from radical polymers, polycondensates and polymers of synthetic origin.

54. The make-up kit according to claim 42, wherein the first film-forming polymer and the at least one second film-forming polymer are independently selected from vinyl polymers, polyurethanes, polyesters and cellulose polymers.

55. The make-up kit according to claim 42, wherein the at least one first film-forming polymer is present in the first composition in an amount ranging from 1% to 70% by weight with respect to the total weight of the first composition.

56. The make-up kit according to claim 55, wherein the at least one first film-forming polymer is present in the first composition in an amount ranging from 10% to 40% by weight with respect to the total weight of the first composition.

57. The make-up kit according to claim 42, wherein the at least one second film-forming polymer is present in the second composition in an amount ranging from 1% to 70% by weight with respect to the total weight of the second composition.

58. The make-up kit according to claim 57, wherein the at least one second film-forming polymer is present in the second composition in an amount ranging from 10% to 40% by weight with respect to the total weight of the second composition.

59. The make-up kit according to claim 42, wherein at least one of the first composition and the second composition additionally comprise at least one coloring material chosen from dyes and pulverulent coloring materials having a particle size of less than or equal to 70 µm.

60. The make-up kit according to claim 42, wherein the first composition comprises at least one coloring material selected from dyes and pulverulent coloring materials having a particle size of less than or equal to 70 µm.

61. The make-up kit according to claim 42, wherein the second composition comprises a substantially translucent medium.

62. The make-up kit according to claim 42, wherein at least one of the first composition and the second composition additionally comprise at least one additive chosen from additional agents which are able to form a film, thickening agents, spreading agents, wetting agents, dispersing agents, anti-foaming agents, preservatives, UV screening agents, active principles, surfactants, moisturizing agents, fragrances, neutralizing agents, stabilizing agents and anti-oxidants.

63. The make-up kit according to claim 42, wherein at least one of the first composition and the second composition are in the form of a nail varnish, face powder, eye shadow, foundation or product for making up lips or body.

64. The make-up kit according to claim 42, wherein the kit comprises means for applying the first and the second compositions to keratinous substances.

65. A made-up substrate comprising on said substrate a make-up composition comprising, in a cosmetically acceptable medium:

a film-forming polymer and a coloring material, wherein the coloring material comprises at least one colored polymer film fragment which exhibits two substantially flat faces, which has a thickness ranging from 40 to 200 µm and which has a larger dimension ranging from 0.1 to 4 mm, the at least one colored polymer film fragment being insoluble in a medium of the composition, wherein the make-up composition is applied on a substrate.

66. The substrate according to claim 65, wherein the substrate is in the form of false nails or of postiches.

67. A made-up substrate comprising obtained by the step comprising:

applying, to the keratinous substance, at least one layer of a composition comprising, in a cosmetically acceptable medium:

a film-forming polymer and a coloring material, wherein the coloring material comprises at least one colored polymer film fragment which exhibits two substantially flat faces, which has a thickness ranging from 40 to 200 µm and which has a larger dimension ranging from 0.1 to 4 mm, the at least one colored polymer film fragment being insoluble in a medium of the composition.

68. A made-up substrate comprising obtained by the step comprising:

applying to the keratinous substance:

a first layer of a first composition comprising, in a cosmetically acceptable medium, a first film-forming polymer, and then, to at least a portion of the first layer, a second layer of a second composition comprising at least one second film-forming polymer in a cosmetically acceptable medium and at least one coloring material comprising at least one colored polymer film fragment which exhibits two substantially flat faces, which has a thickness ranging from 40 to 200 µm and which has a larger dimension ranging from 0.1 to 4 mm, the fragment being insoluble in the medium of the composition, wherein the first composition does not comprise the at least one colored polymer film fragment.

* * * * *

UNITED STATES PATENT AND TRADEMARK OFFICE
CERTIFICATE OF CORRECTION

PATENT NO.   : 6,447,761 B1
DATED        : September 10, 2002
INVENTOR(S)  : Roland Ramin It is certified that error appears in the above-identified patent and that said Letters Patent is hereby corrected as shown below:

Column 9,
Lines 44 and 50, after "according" insert -- to --.

Signed and Sealed this

Fourth Day of February, 2003

JAMES E. ROGAN
*Director of the United States Patent and Trademark Office*